(12) United States Patent
Li et al.

(10) Patent No.: US 8,980,050 B2
(45) Date of Patent: *Mar. 17, 2015

(54) METHODS FOR REMOVING HEMICELLULOSE

(71) Applicant: Celanese International Corporation, Irving, TX (US)

(72) Inventors: Rongfu Li, Blacksburg, VA (US); Jay Mehta, Blacksburg, VA (US); Xiaoyan Tu, Blacksburg, VA (US); Prabuddha Bansal, Blacksburg, VA (US); Michael Combs, Shady Spring, WV (US); Denis Fallon, Blacksburg, VA (US); Lawton E Kizer, Blacksburg, VA (US)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/827,837

(22) Filed: Mar. 14, 2013

(65) Prior Publication Data

US 2014/0048222 A1 Feb. 20, 2014

Related U.S. Application Data

(60) Provisional application No. 61/684,973, filed on Aug. 20, 2012.

(51) Int. Cl.
*D21C 11/00* (2006.01)

(52) U.S. Cl.
USPC ............ 162/14; 162/17; 162/19; 162/37; 162/141

(58) Field of Classification Search
USPC ............ 162/14, 17, 19, 37, 72–76, 141, 234; 530/500; 536/123.1, 56
See application file for complete search history.

(56) References Cited

U.S. PATENT DOCUMENTS

| | | | |
|---|---|---|---|
| RE23,868 E | 9/1954 | Limerick | |
| 4,246,221 A | 1/1981 | McCorsley, III | |
| 5,362,867 A | 11/1994 | Chin et al. | |
| 5,540,874 A | 7/1996 | Yamada et al. | |
| 5,584,919 A | 12/1996 | Lee et al. | |
| 5,603,883 A | 2/1997 | Zikeli | |
| 5,626,810 A | 5/1997 | Zikeli et al. | |
| 5,676,795 A | 10/1997 | Wizani et al. | |
| 5,693,279 A | 12/1997 | Feuer et al. | |
| 5,760,211 A | 6/1998 | Schleicher et al. | |
| 5,891,375 A | 4/1999 | Stall et al. | |
| 5,948,905 A | 9/1999 | Connor et al. | |
| 5,951,933 A | 9/1999 | Stall et al. | |
| 6,057,438 A | 5/2000 | Hyatt et al. | |
| 6,207,601 B1 | 3/2001 | Maurer et al. | |
| 6,210,801 B1 | 4/2001 | Luo et al. | |
| 6,211,358 B1 | 4/2001 | Honda et al. | |
| 6,248,267 B1 | 6/2001 | Hosako et al. | |
| 6,482,940 B1 | 11/2002 | Klohr et al. | |
| 6,548,660 B2 | 4/2003 | Sato et al. | |
| 6,555,678 B1 | 4/2003 | Allandrieu et al. | |
| 6,610,134 B1 | 8/2003 | Kind et al. | |
| 6,677,447 B1 | 1/2004 | Lee et al. | |
| 6,773,497 B2 | 8/2004 | Katai | |
| 6,808,557 B2 | 10/2004 | Holbrey et al. | |
| 6,812,270 B2 | 11/2004 | Lee et al. | |
| 6,824,599 B2 | 11/2004 | Swatloski et al. | |
| 6,852,229 B2 | 2/2005 | Mehnert et al. | |
| 6,897,303 B2 | 5/2005 | Yamada | |
| 6,939,960 B2 | 9/2005 | Klohr et al. | |
| 7,005,427 B2 | 2/2006 | Ito et al. | |
| 7,074,919 B2 | 7/2006 | Aubay et al. | |
| 7,122,660 B1 | 10/2006 | Nakanishi et al. | |
| 7,148,344 B2 | 12/2006 | Nakanishi et al. | |
| 7,214,335 B2 | 5/2007 | Kwon et al. | |
| 7,550,520 B2 | 6/2009 | Daly et al. | |
| 7,585,392 B2 | 9/2009 | Kokko et al. | |
| 7,674,608 B2 | 3/2010 | Varanasi et al. | |
| 7,714,124 B2 | 5/2010 | Scheibel et al. | |
| 7,718,036 B2 | 5/2010 | Sumnicht et al. | |
| 7,749,318 B2 | 7/2010 | Maase et al. | |
| 7,754,002 B2 | 7/2010 | Maase et al. | |
| 7,828,936 B2 | 11/2010 | Luo et al. | |
| 7,842,637 B2 | 11/2010 | Ebron et al. | |
| 7,998,313 B2 | 8/2011 | Kokko | |
| 8,030,030 B2 | 10/2011 | Varanasi et al. | |
| 8,044,120 B2 | 10/2011 | D'Andola et al. | |
| 8,067,488 B2 | 11/2011 | Buchanan et al. | |
| 2005/0288484 A1 | 12/2005 | Holbrey et al. | |

(Continued)

FOREIGN PATENT DOCUMENTS

| | | |
|---|---|---|
| CN | 1417407 A | 5/2003 |
| CN | 1986534 | 6/2007 |

(Continued)

OTHER PUBLICATIONS

Zhou et al., "Acetate-grade pulp from birch", BioResources, (2010), 5(3), 1779-1788.
S. Zhu et al., Green Chem. 2006, 8, pp. 325-327.
Froschauer, et al., "Separation of Hemicellulose and Cellulose from Wood Pulp by Means of Ionic Liquid/Cosolvent Systems", BioMacromolecules, 14, 2013, pp. 1741-1750.
International Search Report and Written Opinion for PCT/US2013/055832 mailed Oct. 9, 2013.
Kuo, et al., "Enhanced enzymatic hydrolysis of sugarcane bagasse by N-methylmorpholine-N-oxide pretreatment", Bioresource Technology, vol. 100, No. 2, Jan. 1, 2009, pp. 866-871.
Shafiei, et al., "Pretreatment of spruce and oak by N-methylmorpholine-N-oxide (NMMO) for efficient conversion of their cellulose to ethanol", Bioresource Technology, vol. 101, No. 13, Jul. 1, 2010, pp. 4914-4918.
Kuo, et al., "Enhancement of enzymatic saccharification of cellulose by cellulose dissolution pretreatments", Carbohydrate Polymers, Applied Science Publishers, vol. 77, No. 1, May 22, 2009, pp. 41-46.
Ramakrishnan, et al., "Enzymatic hydrolysis of cellulose dissolved in N-methylmorphine oxide/water solutions", Bioresource Technology, vol. 101, No. 13, Jul. 1, 2010, pp. 4965-4970.

(Continued)

*Primary Examiner* — Mark Halpern (57) ABSTRACT

A method for treating a cellulosic material comprising extracting the cellulosic material with an extractant to selectively extract hemicellulose therein and separating the extracted hemicellulose to form a cellulosic product comprising less hemicellulose than the cellulosic material. The extractant comprises an amine oxide and a non-solvent. The cellulosic product retains the cellulosic fiber morphology.

28 Claims, 3 Drawing Sheets

(56) References Cited

U.S. PATENT DOCUMENTS

| | | |
|---|---|---|
| 2007/0006774 A1 | 1/2007 | Rogers et al. |
| 2007/0073051 A1 | 3/2007 | Myllymaki et al. |
| 2007/0112185 A1 | 5/2007 | Myllymaki et al. |
| 2007/0215300 A1 | 9/2007 | Upfal et al. |
| 2008/0023162 A1 | 1/2008 | Myllymaki et al. |
| 2008/0135193 A1 | 6/2008 | Kokko |
| 2008/0173418 A1 | 7/2008 | Sumnicht |
| 2008/0173419 A1 | 7/2008 | Sumnicht |
| 2008/0190013 A1 | 8/2008 | Argyropoulos |
| 2008/0194807 A1 | 8/2008 | Buchanan et al. |
| 2008/0194808 A1 | 8/2008 | Buchanan et al. |
| 2008/0194834 A1 | 8/2008 | Buchanan et al. |
| 2008/0241536 A1 | 10/2008 | Luo et al. |
| 2008/0269477 A1 | 10/2008 | Stegmann et al. |
| 2009/0020112 A1 | 1/2009 | Massonne et al. |
| 2009/0020139 A1 | 1/2009 | Sumnicht et al. |
| 2009/0020248 A1 | 1/2009 | Sumnicht et al. |
| 2009/0062524 A1 | 3/2009 | Massonne et al. |
| 2009/0084509 A1 | 4/2009 | Luo et al. |
| 2009/0093027 A1 | 4/2009 | Balan et al. |
| 2009/0182138 A1 | 7/2009 | Massonne et al. |
| 2009/0187016 A1 | 7/2009 | Massone et al. |
| 2009/0203898 A1 | 8/2009 | Buchanan et al. |
| 2009/0203899 A1 | 8/2009 | Buchanan et al. |
| 2009/0203900 A1 | 8/2009 | Buchanan et al. |
| 2009/0221813 A1 | 9/2009 | Moellmann et al. |
| 2009/0258227 A1 | 10/2009 | Ebeling et al. |
| 2009/0258561 A1 | 10/2009 | Ebeling et al. |
| 2009/0259032 A1 | 10/2009 | Ebeling et al. |
| 2009/0270608 A1 | 10/2009 | Zhang et al. |
| 2009/0281303 A1 | 11/2009 | Massonne et al. |
| 2009/0326216 A1 | 12/2009 | Stegmann et al. |
| 2010/0004437 A1 | 1/2010 | Binder et al. |
| 2010/0006249 A1 | 1/2010 | Kokko et al. |
| 2010/0029927 A1 | 2/2010 | Buchanan et al. |
| 2010/0048829 A1 | 2/2010 | D'Andola et al. |
| 2010/0081798 A1 | 4/2010 | Balensiefer et al. |
| 2010/0081833 A1 | 4/2010 | Gruter et al. |
| 2010/0092419 A1 | 4/2010 | Guerrero-Sanchez et al. |
| 2010/0112646 A1 | 5/2010 | Balensiefer et al. |
| 2010/0163018 A1 | 7/2010 | Gifford et al. |
| 2010/0170504 A1 | 7/2010 | Zhang |
| 2010/0174060 A1 | 7/2010 | Kwon et al. |
| 2010/0196692 A1 | 8/2010 | Lodha et al. |
| 2010/0196967 A1 | 8/2010 | Edye et al. |
| 2010/0212850 A1 | 8/2010 | Sumnicht et al. |
| 2010/0215988 A1 | 8/2010 | Daly et al. |
| 2010/0222460 A1 | 9/2010 | HoJo |
| 2010/0233773 A1 | 9/2010 | Varanasi et al. |
| 2010/0234586 A1 | 9/2010 | O'Connor et al. |
| 2010/0239673 A1 | 9/2010 | Linhardt et al. |
| 2010/0248572 A1 | 9/2010 | Firgo et al. |
| 2010/0256352 A1 | 10/2010 | Uerdingen et al. |
| 2010/0267942 A1 | 10/2010 | Buchanan et al. |
| 2010/0272819 A1 | 10/2010 | Engelhardt et al. |
| 2010/0279372 A1 | 11/2010 | Cho et al. |
| 2010/0305249 A1 | 12/2010 | Buchanan et al. |
| 2010/0323930 A1 | 12/2010 | Champ et al. |
| 2010/0331222 A1 | 12/2010 | Braun et al. |
| 2010/0331560 A1 | 12/2010 | Borden |
| 2011/0009259 A1 | 1/2011 | Innerlohinger et al. |
| 2011/0015387 A1 | 1/2011 | Schuth et al. |
| 2011/0045078 A1 | 2/2011 | Kolbe et al. |
| 2011/0073805 A1 | 3/2011 | Dibble et al. |
| 2011/0175023 A1 | 7/2011 | Granstrom et al. |
| 2011/0180751 A1 | 7/2011 | Rein et al. |
| 2011/0196139 A1 | 8/2011 | Lee et al. |
| 2011/0201096 A1 | 8/2011 | Streffer |
| 2011/0207182 A1 | 8/2011 | Sapra et al. |
| 2011/0226427 A1 | 9/2011 | Chou et al. |
| 2011/0230655 A1 | 9/2011 | Moulijn et al. |
| 2011/0245062 A1 | 10/2011 | Hayakawa |
| 2011/0251377 A1 | 10/2011 | Rahman et al. |
| 2011/0293732 A1 | 12/2011 | Nachtkamp et al. |
| 2011/0306760 A1 | 12/2011 | Buchanan et al. |
| 2013/0012610 A1 | 1/2013 | Belanger et al. |
| 2013/0292331 A1 | 11/2013 | Lipscomb et al. |
| 2014/0048221 A1 | 2/2014 | Li et al. |
| 2014/0048223 A1 | 2/2014 | Li et al. |
| 2014/0073017 A1 | 3/2014 | Kaper et al. |

FOREIGN PATENT DOCUMENTS

| | | |
|---|---|---|
| CN | 101012319 | 8/2007 |
| CN | 101050195 | 10/2007 |
| CN | 101463137 | 6/2009 |
| CN | 101580549 A | 11/2009 |
| CN | 101613479 | 12/2009 |
| CN | 101613893 | 12/2009 |
| CN | 101701428 | 5/2010 |
| CN | 101880410 | 11/2010 |
| CN | 101906233 | 12/2010 |
| CN | 102409572 | 4/2012 |
| CN | 102443235 | 5/2012 |
| CN | 102492163 | 6/2012 |
| CN | 103059280 | 4/2013 |
| CN | 103290504 | 9/2013 |
| CN | 103509123 | 1/2014 |
| CN | 103613672 | 3/2014 |
| DE | 19624867 A1 | 12/1997 |
| EP | 0771902 A1 | 5/1997 |
| EP | 2199319 A1 | 6/2010 |
| JP | 2008-303319 A | 12/2008 |
| WO | WO 2007/032022 A2 | 3/2007 |
| WO | WO 2009/030950 A1 | 3/2009 |
| WO | WO 2010/020649 A1 | 2/2010 |
| WO | WO 2010/034055 A1 | 4/2010 |
| WO | WO 2010/056790 A1 | 5/2010 |
| WO | WO 2011/114004 A1 | 9/2011 |
| WO | WO 2011/141470 A2 | 11/2011 |
| WO | WO 2011/154370 A1 | 12/2011 |
| WO | WO 2012/004582 A1 | 1/2012 |
| WO | WO 2012/004583 A1 | 1/2012 |
| WO | WO 2012/025228 A1 | 3/2012 |
| WO | WO 2013/171364 | 11/2013 |
| WO | WO 2014/060651 | 4/2014 |

OTHER PUBLICATIONS

Office Action for U.S. Appl. No. 13/827,767 dated Apr. 17, 2014.
Froschauer, et al., "Diakyl Phosphate-Related Ionic Liquids as Selective Solvents for Xylan", Apr. 16, 2012, Niomacromolecules, 1973-1980.
Sixta et al., "Novel concepts of dissolving pulp production", 2013, Cellulose, 20, 1547-1561.
ChemLab, Monoprotic and polyprotic acids, May 24, 2010.
Deng et al., "Preparation of nanoporous cellulose foams from celluolse-ionic liquid solutions" Materials Letters (2009) 63(21), 1851-1854.—Abstract.
Fan et al., "Hydrolysis of cellulose catalyzed by sulfonated poly(stryene-co-divinylbenzene) in the ionic liquid 1-n-butyl-3-methylimidazolium bromide" Fuel Processing Technology (2013) 116, 142-148.—Abstract.
Jiang et al., "Isolution of cellulose with ionic liquid from stream exploded rice straw" Industrial Crops and Products (2011) 33(3) 734-738.—Abstract.
Li et al., "Research progress on dissolution and functional modification of cellulose in ionic liquids" Journal of Molecular Liquids (2008) 142 (1-3), 1-5.—Abstract.
Li et al., "A novel cellulose hydrogel prepared from its ionic liquid solution" Chinese Science Bulletin (2009), 54(9), 1622-1625.—Abstract.
Lu et al., "Advance in solvents of cellulose" Gaofenze Xuebao (2007) (10) 937-944.—Abstract.
Michael, et al., "Interaction of Cellulose with Amine Oxide Solvents", Cellulose, 7, 2000, pp. 21-33.
Sixta, Herbert et al., Advances in Dissolving Pulp Technology; 6th ICEP, Colonia del Sacramento, Uruguay, Nov. 27, 2013.—Abstract.
Sun et al., "Acetone-soluble cellulose acetate extracted from waste blended fabrics via ionic liquid catalyzed acetylation" Carbohydrate Polymers (2013) 98(1), 405-411.—Abstract.

(56) References Cited

OTHER PUBLICATIONS

Testova et al., Isolation of Hemicelluloses from Birch Wood: Distribution of Wood Components and Preliminary Trials in Dehydration of Hemicelluloses; Lenzinger Berichte 87 (2009) 58-65.
Wang et al., "Structure and properties of activated bacterial cellulose" Gongneng Cailiao (2012), 43(14), 1945-1949.—Abstract.
Wang et al., "Comparison on the dissolution characteristics among new solvents of cellulose" Fangzhi Keji Jinzgan (2008), (1), 11-13, 19.—Abstract.
Wang et al., "Swelling behaviors of natural cellulose in ionic liquid aqueous solutions" Journal of Applied Polymer Science (2014) 131 (9) 40119/1-40119/6.—Abstract.
Wu et al., "Green composite films prepared from cellulose, starch and lignin in room-temperature ionic liquid" Bioresource Technology (2009) 100(9), 2569-2574.—Abstract.
Xu et al., "Dissolving bacterial cellulose in room temperature ionic liquid" Gongneng Gaofenzi Xuebao (2009) 22(4), 349-355.—Abstract.
Zhang et al., "Efficient acid-catalyzed hydrolysis of cellulose in organic electrolyte solutions" Polymer Degradation and Stability (2012), 97(4), 573-577.—Abstract.
Zhang et al., "A new application of ionic liquids for heterogeneously catalyzed acetylation of cellulose under solvent-free conditions" RSC Advances (2013), 3 (21), 7722-7725.—Abstract.
Office Action for U.S. Appl. No. 13/827,881 dated Jan. 13, 2014.
Notice of Allowance for U.S. Appl. No. 13/827,881 dated Mar. 6, 2014.
Zhou, et al., "Progress on homogeneously chemical modification of cellulose" Zhongguo Kexue: Hauxue (2012) 42(5), 591-605.—Abstract.
Response to Office Action dated Jan. 13, 2014 for U.S. Appl. No. 13/827,881, filed Feb. 12, 2014.
Response and RCE for U.S. Appl. No. 13/827,881, filed Jun. 5, 2014.
Office Action for U.S. Appl. No. 13/827,881 dated Jul. 29, 2014.

METHODS FOR REMOVING HEMICELLULOSE

CROSS-REFERENCE TO RELATED APPLICATION

This is a non-provisional of U.S. Provisional Application 61/684,973, filed Aug. 20, 2012, the entirety of which is incorporated herein by reference.

FIELD OF THE INVENTION

The present invention relates generally to the removal of hemicellulose from cellulose containing materials. In particular, the present invention relates to methods for extracting hemicellulose from cellulose containing materials.

BACKGROUND OF THE INVENTION

Cellulose is typically obtained from wood pulp and cotton and may be further modified to create other derivatives including cellulose ethers, cellulose esters and cellulose nitrate, among others. Cellulose derivatives have a variety of commercial uses. For example, cellulose acetate is the acetate ester of cellulose and is used for a variety of products, including textiles (e.g., linings, blouses, dresses, wedding and party attire, home furnishings, draperies, upholstery and slip covers), industrial uses (e.g., cigarette and other filters for tobacco products, and ink reservoirs for fiber tip pens, decking lumber), high absorbency products (e.g., diapers, sanitary napkins, and surgical products), thermoplastic products (e.g., film applications, plastic instruments, and tape), cosmetic and pharmaceutical (extended capsule/tablet release agents and encapsulating agent), medicinal (hypoallergenic surgical products) and others.

High purity α-cellulose is required as a starting material to make cellulose derivatives, such as cellulose acetate. Acetate-grade pulps are specialty raw materials produced in commercial pulp processes, but the cost for such pulps is high. Commercial paper grade pulps contain less than 90% α-cellulose and are potential crude cellulosic sources for making cellulose derivatives. However, paper grade pulp also contains a high amount of impurities, such as hemicellulose, rendering it incompatible with certain industrial uses, such as making acetate flake or tow.

Zhou et al. discusses the use of dimethyldioxirane (DMDO), a pulp bleaching agent, to treat birch pulp and obtain acetate-grade pulp. However, DMDO is not commercially available due to its instability. Therefore, it is not an ideal solvent for producing large quantities of high α-cellulose pulp. Zhou et al. "Acetate-grade pulp from birch," BioResources, (2010), 5(3), 1779-1778.

Studies have been done regarding the treatment of biomass to form biofuels. Specifically, it is known that various ionic liquids can be used to dissolve cellulosic material. S. Zhu et al. in Green Chem. 2006, 8, pp. 325-327, describe the possibility of dissolving cellulose in ionic liquids and recovering it by addition of suitable precipitates such as water, ethanol, or acetone.

Others have used ionic liquids to break down the cellulosic materials to make biofuels by way of glucose. For example, US Pat. Appl. 2010/0112646 discloses a process for preparing glucose from a cellulosic material, in which a cellulose-comprising starting material is provided and treated with a liquid treatment medium comprising an ionic liquid and an enzyme. Similarly, US Pat. Appl. 2010/0081798 discloses a process for preparing glucose from a material containing ligno-cellulose, in which the material is first treated with an ionic liquid and then subjected to enzymatic hydrolysis. US Pat. Appl. 2010/0081798 describes obtaining glucose by treating a material containing lingo-cellulose with an ionic liquid and subjecting same to an enzymatic hydrolysis and fermentation. However, in order to turn cellulose containing materials into glucose, the methods disclosed in these references result in breaking down the cellulose molecules, making them unsuitable for use as starting materials to make cellulose derivatives.

U.S. Pat. No. 7,828,936 describes a method for dissolving cellulose in which the cellulose based raw material is admixed with a mixture of a dipolar aprotic intercrystalline swelling agent and an ionic liquid. This method results in the complete dissolution of the cellulose and destruction of the fiber morphology of the cellulose. Although the cellulose may be regenerated using a non-solvent, the crystallinity of the regenerated cellulose is lower than the original cellulose sample.

Therefore the need exists for methods for producing high purity α-cellulose from lower grade starting materials without destroying the fiber morphology and other characteristics of the cellulose structure. In particular, the need exists for cost effective methods for removing hemicellulose from cellulosic materials to recover high purity α-cellulose that can be converted to other cellulose derivatives.

SUMMARY OF THE INVENTION

In a first embodiment, the present invention is directed to a method for treating a cellulosic material. The method comprises the step of extracting the cellulosic material with an extractant to selectively dissolve hemicellulose. Preferably, the extractant comprises an amine oxide and a non-solvent. In an embodiment, the non-solvent is water, DMSO, or a combination thereof. The method further comprises the step of separating the dissolved hemicellulose from the cellulosic material to form a cellulosic product, which comprises less hemicellulose than the cellulosic material. Preferably, the extractant selectively dissolves at least 20% of hemicellulose in the cellulosic material. Preferably, less than 20% of the cellulose in the cellulosic material is dissolved. Preferably, the cellulosic product retains a cellulosic fiber morphology.

In a second embodiment, the present invention is directed to a method for producing high purity α-cellulose grade pulp. The method comprises the step of extracting hemicellulose from a wood pulp by treating the wood pulp with an extractant comprising an amine oxide and a non-solvent to form an intermediate wood pulp that retains a cellulosic fiber morphology and other suitable characteristic such as intrinsic viscosity and brightness. The method further comprises treating the intermediate wood pulp with an enzyme to hydrolyze the hemicellulose contained therein to form a reduced hemicellulose wood pulp. The method further comprises the step of washing the reduced hemicellulose wood pulp with a wash solution to form the high purity α-cellulose grade pulp. In an embodiment, the wash solution is selected from the group consisting of DMSO, N-methylpyrrolidone, DMF, methanol, ethanol, isopropanol, dimethyl carbonate, acetone and/or water.

In a third embodiment, the present invention is directed to a solvent system for selectively reducing hemicellulose in a cellulosic material to form a reduced hemicellulose cellulosic product. Preferably, the solvent system comprises 50-80 wt. % amine oxide and 20-50 wt. % water. In one embodiment, the solvent system further comprises DMSO, DMF, or a mixture thereof.

In a fourth embodiment, the present invention is directed to a solvent system for selectively reducing hemicellulose in a cellulosic material to form a hemicellulose reduced cellulosic product. Preferably, the solvent comprises at most 40 wt. % amine oxide, at most 12.5 wt. % water, and at least 50 wt. % DMSO.

BRIEF DESCRIPTION OF THE DRAWINGS

The present invention will be better understood in view of the appended non-limiting figures, in which.

DETAILED DESCRIPTION OF THE INVENTION

Introduction

The present invention is directed to methods suitable for removing impurities, such as hemicellulose, from a cellulosic material. Generally speaking, the term "cellulosic material" includes cellulose and hemicellulose. The process of the invention generally include a step of selectively extracting hemicellulose from a cellulosic material using an extractant. Preferably, the extractant includes an amine oxide and a non-solvent. The extracted hemicellulose is then separated from the cellulosic product. As a result, the cellulosic product has less hemicellulose than the starting cellulosic material, e.g., at least 10% less, at least 20% less or at least 30% less hemicellulose than the cellulosic material.

In one embodiment, the cellulosic material may be subjected to one or more extractions with an extractant. The extractant includes an amine oxide that is suitable for dissolving the cellulosic material. It is known that amine oxides, such as N-methylmorpholine-N-oxide (NMMO), typically can be used to dissolve the α-cellulose in the Lyocell process to produce cellulose fibers. As a result of the dissolution of cellulose, the fiber morphology of the cellulosic material is destroyed. Once destroyed, the original fiber morphology of the cellulose disappears and cannot be regenerated. It has now been discovered that by using a mixture of NMMO and non-solvent at appropriate proportions, hemicellulose may be selectively dissolved without dissolving α-cellulose. As a result, the fiber morphology of the cellulosic material is retained in the cellulosic product. Without being bound by theory, α-cellulose is generally insoluble in the amine oxide/non-solvent extractant, while hemicellulose is soluble therein. As used herein, the term "non-solvent" refers to liquids that are capable of reducing α-cellulose solubility in amine oxides to a point that the α-cellulose does not readily dissolve in a mixture of the non-solvent with an amine oxide. Therefore, the non-solvent in combination with the amine oxide selectively dissolves the hemicellulose but leaves the cellulose substantially intact. In addition, other characteristics of the cellulosic material are also retained, such as intrinsic viscosity and brightness. Thus, the resulting cellulosic product has a reduced amount of hemicellulose, but retains the fiber morphology, intrinsic viscosity and brightness of the cellulosic material. In one embodiment, less than 15% of the cellulose in the cellulosic material is extracted, e.g., less than 10%, or less than 5%, as determined by HPLC based carbohydrate analysis. In one embodiment, the cellulosic material may be subjected to repeated extraction with the extractant.

In one embodiment, the cellulosic material may also be treated with an enzyme to hydrolyze the hemicellulose to form a reduced hemicellulose product. It has now been discovered that by treating cellulosic materials with both the extractant and an enzyme, a substantially hemicellulose-free cellulosic product may be recovered. For example, the cellulosic product may comprise less than 5% hemicellulose, less than 3% hemicellulose, or less than 2% hemicellulose. Surprisingly and unexpectedly, the order of extractant and enzyme treatments of the cellulosic material affects the amount of hemicellulose removed from the cellulosic material. In preferred embodiments, the cellulosic material is treated with the extractant prior to enzyme treatment (although the reverse sequence of steps is also contemplated). In one embodiment, the cellulosic material may be treated with the extractant again after the enzyme treatment, optionally followed by another enzyme treatment step. The extractant and enzyme treatment steps may be further repeated as desired to obtain the desired α-cellulose purity.

In one embodiment, the non-solvent may be an organic solvent or an aqueous solvent. In one embodiment, the non-solvent may be selected from water, dimethylformamide (DMF), dimethyl sulfoxide (DMSO), methanol, ethanol, isopropanol, acetone, acetic acid, and mixtures thereof.

In one embodiment, solvents may be used to wash and remove the amine oxide from the cellulose product. For example, DMSO, DMF, methanol, ethanol, isopropanol, acetone, dimethyl carbonate or mixtures thereof may be used as a washing agent for the cellulosic material.

In another embodiment, acetone and/or water may be used as a rinsing agent to remove other solvents from the reduced hemicellulose product before drying to produce the final cellulose product.

Process for Removing Hemicellulose

The present invention is broadly applicable to the treatment of natural cellulose-containing materials, including plant and plant-derived materials. As used herein, the term "cellulose-containing material" includes, without limitation, plant derived biomass, corn stover, sugar cane bagasse and cane residues, rice and wheat straw, agricultural grasses, woodchips, and other forms of wood, bamboo, and all other materials proximately or ultimately derived from plants.

Generally, cellulosic material may be derived from lignin-containing materials, where lignin has been removed therefrom. In cellulosic materials, hemicellulose is linked to cellulose by hydrogen bonds. Overall, the cellulosic material has a linear shape of fiber morphology, which is surrounded by hemicellulose via hydrogen bonds. These bonds between cellulose and hemicellulose may become weakened by treating the cellulosic material with an extractant to selectively dissolve the hemicellulose while maintaining the fiber morphology of the cellulosic material.

The cellulosic material may be provided as pellets, sheets or chips. Exemplary sources of cellulosic material include, but are not limited to, rice straw, hard wood, hardwood pulp, soft wood, softwood pulp, herbs, recycled paper, waste paper, wood chips, pulp and paper wastes, waste wood, thinned wood, cornstalk, chaff, wheat straw, sugar cane stalk, bagasse, agricultural residual products, agricultural wastes, excretions of livestock, or mixtures thereof. In one embodiment of the invention, the cellulosic material is a paper grade pulp provided in forms such as, but not limited to, rolls, sheets, or bales. Preferably, the paper grade pulp comprises at least 70 wt. % α-cellulose, e.g., at least 80 wt. % α-cellulose or at least 85 wt. % α-cellulose. Paper grade pulp typically also comprises at least 5 wt. % hemicellulose, at least 10 wt. % hemicellulose or at least 15 wt. % hemicellulose. In another embodiment, the cellulosic material may be other α-cellulose containing pulps, such as viscose grade pulp, rayon grade pulp, semi-bleached pulp, unbleached pulp, bleach pulp, Kraft pulp, absorbent pulp, dissolving, or fluff. These cellulosic materials may be treated using the inventive method to produce high purity α-cellulose products.

Cellulose is a straight chain polymer and is derived from D-glucose units, which condense through β-1,4-glycosidic bonds. This linkage motif contrasts with that for α-1,4-glycosidic bonds present in starch, glycogen, and other carbohydrates. Unlike starch, there is no coiling or branching in cellulose and cellulose adopts an extended and rather stiff rod-like confirmation, which is aided by the equatorial confirmation of the glucose residues. The multiple hydroxyl groups on the glucose from one chain form hydrogen bonds with oxygen atoms on the same or on a neighboring chain, holding the chains firmly together side-by-side and forming microfibrils with high tensile strength, which then overlay to form the macrostructure of a cellulose fiber. In an embodiment of the invention, the cellulosic product retains the fiber structure after the extraction of hemicellulose.

Hemicellulose is a polysaccharide that is typically present along with cellulose in almost all plant cell walls. Hemicellulose can be any one of xylan, glucuronoxylan, arabinoxylan, glucomannan, galactomannan, and xyloglucan. These polysaccharides contain many different sugar monomers and can be hydrolyzed.

The process of the present invention is particularly beneficial in that it has shown to be effective for use with paper grade wood pulp that is derived from softwoods and hardwoods. The method of the present invention provides a potential technique for upgrading paper grade pulp produced from softwood species, which are generally more abundant, and faster growing, than most hardwood species.

Softwood is a generic term typically used in reference to wood from conifers (i.e., needle-bearing trees from the order Pinales). Softwood-producing trees include pine, spruce, cedar, fir, larch, douglas-fir, hemlock, cypress, redwood and yew. Conversely, the term hardwood is typically used in reference to wood from broad-leaved or angiosperm trees. The terms "softwood" and "hardwood" do not necessarily describe the actual hardness of the wood. While, on average, hardwood is of higher density and hardness than softwood, there is considerable variation in actual wood hardness in both groups, and some softwood trees can actually produce wood that is harder than wood from hardwood trees. One feature separating hardwoods from softwoods is the presence of pores, or vessels, in hardwood trees, which are absent in softwood trees. On a microscopic level, softwood contains two types of cells, longitudinal wood fibers (or tracheids) and transverse ray cells. In softwood, water transport within the tree is via the tracheids rather than the pores of hardwoods.

Extractant

The extractant for dissolving the cellulosic material may be any extractant capable of dissolving at least 50% of the hemicellulose, preferably at least 75% or at least 90% of the hemicellulose, in the cellulosic material. The extractant should not over-degrade the cellulose. For example, in one embodiment, the extractant dissolves less than 15% of the α-cellulose in the cellulosic material, e.g., less than 10%, or less than 5%.

In accordance to the present invention, the extractant comprises two or more components. According to the invention, the extractant comprises at least an amine oxide and a non-solvent. In one embodiment, the extractant further includes a second non-solvent. The amine oxide is preferably capable of penetrating the cellulosic material. As discussed above, the amine oxide is capable of dissolving both α-cellulose and hemicellulose. The non-solvent as used in accordance with the present invention reduces α-cellulose solubility in the amine oxide to a point that the α-cellulose does not readily dissolve in a mixture of the non-solvent with the amine oxide. Preferably, the α-cellulose is insoluble in the non-solvent. The extractant in accordance with the present invention, therefore, has the property of selectively dissolving the hemicellulose that is in the cellulosic material.

Without being bound by theory, the insolubility of the α-cellulose in the non-solvent and the extraction agent maintains the cellulose fiber morphology, while the extractant penetrates the cellulosic material and dissolves and extracts the hemicellulose from the cellulosic material. Depending on the specific non-solvent used in the extractant, the weight percentage of the amine oxide and the non-solvent in the extractant may vary widely.

In one embodiment, the extractant comprises at least 0.8 wt. % amine oxide, e.g., at least 2 wt. % or at least 4 wt. %. In terms of upper limits, the extractant may comprise at most 95 wt. % amine oxide, e.g., at most 90 wt. %, or at most 85 wt. %. In terms of ranges, the extractant may comprise from 0.8 wt. % to 95 wt. % amine oxide, e.g., from 2 wt. % to 90 wt. %, or from 4 wt. % to 80 wt. %. The extractant may comprise at least 0.1 wt. % non-solvent, e.g., at least 0.3 wt. %, or at least 0.6 wt. %. In terms of upper limits, the extractant may comprise at most 99.9 wt. %, at most 98 wt. %, or at most 97 wt. %. In terms of ranges, the extractant may comprise from 0.1 wt. % to 99.9 wt. % non-solvent, e.g., from 0.3 wt. % to 98 wt. %, or from 0.6 wt. % to 97 wt. %.

In one embodiment, the extractant comprises an aqueous non-solvent and an amine oxide. The extractant comprises at least 50 wt. % amine oxide, e.g., at least 65 wt. % or at least 80 wt. %. In terms of upper limits, the extractant may comprise at most 95 wt. % amine oxide, e.g., at most 90 wt. %, or at most 85 wt. %. In terms of ranges, the extractant may comprise from 50 wt. % to 95 wt. % amine oxide, e.g., from 65 wt. % to 90 wt. %, or from 70 wt. % to 85 wt. %. The extractant may comprise at least 5 wt. % aqueous non-solvent, e.g., at least 10 wt. %, or at least 15 wt. %. In terms of upper limits, the extractant may comprise at most 50 wt. % aqueous non-solvent, at most 40 wt. %, or at most 25 wt. %. In terms of ranges, the extractant may comprise from 5 wt. % to 50 wt. % aqueous non-solvent, e.g., from 10 wt. % to 40 wt. %, or from 15 wt. % to 25 wt. %. In one embodiment, the aqueous non-solvent is water.

In one embodiment, when the extractant comprises an organic non-solvent and an amine oxide. The extractant comprises at least 0.1 wt. % amine oxide, e.g., at least 1 wt. % or at least 2 wt. %. In terms of upper limits, the extractant may comprise at most 10 wt. % amine oxide, e.g., at most 8 wt. %, or at most 7 wt. %. In terms of ranges, the extractant may comprise from 0.1 wt. % to 10 wt. % amine oxide, e.g., from 1 wt. % to 8 wt. %, or from 2 wt. % to 7 wt. %. The extractant may comprise at least 90 wt. % organic non-solvent, e.g., at least 93 wt. %, or at least 95 wt. %. In terms of upper limits, the extractant may comprise at most 99.9 wt. % organic non-solvent, at most 98 wt. %, or at most 97 wt. %. In terms of ranges, the extractant may comprise from 90 wt. % to 99.9 wt. % organic non-solvent, e.g., from 93 wt. % to 98 wt. %, or from 95 wt. % to 97 wt. %. In one embodiment, the organic non-solvent is DMSO.

In one embodiment, the extractant includes an amine oxide, a first non-solvent and a second non-solvent. In one embodiment, the extractant includes an amine oxide, an aqueous non-solvent and an organic non-solvent. In one embodiment, the first non-solvent is an aqueous non-solvent and the second non-solvent is an organic non-solvent.

In one embodiment, the extractant includes from 0.01 wt. % to 12.5 wt. % of the first non-solvent, e.g., from 0.33 wt. % to 10 wt. %, or from 0.65 wt. % to 6 wt. %. In terms of lower limits, the extractant may include at least 0.01 wt. % of the first non-solvent, e.g., at least 0.33 wt. %, or at least 0.65 wt. %. In terms of upper limits, the extractant may include at most 12.5 wt. % of the first non-solvent, e.g., at most 10 wt. %, or at most 6 wt. %. In one embodiment, the extractant includes from 50 wt. % to 99.9 wt. % of the second non-solvent, e.g., from 62.5 wt. % to 98 wt. %, or from 75 wt. % to 97 wt. %. In terms of lower limits, the extractant may include at least 50 wt. % of the second non-solvent, e.g., at least 62.5 wt. %, or at least 75 wt. %. In terms of upper limits, the extractant may include at most 99.9 wt. % of the second non-solvent, e.g., at most 98 wt. %, or at most 97 wt. %. In one embodiment, the extractant includes from 0.8 wt. % to 40 wt. % of amine oxide, e.g., from 2 wt. % to 30 wt. %, or from 4 wt. % to 20 wt. %. In terms of lower limits, the extractant may include at least 0.8 wt. % of amine oxide, e.g., at least 2 wt. %, or at least 4 wt. %. In terms of upper limits, the extractant may include at most 40 wt. % of amine oxide, e.g., at most 30 wt. %, or at most 20 wt. %. It has been found that by varying the amount of amine oxide and the first non-solvent, a larger amount of the second non-solvent may be used to extract a maximum amount of hemicellulose from the cellulosic material. In one embodiment, water is the first non-solvent. In one embodiment, DMSO is the second non-solvent. Without being bound by theory, it is postulated that the decrease in viscosity in the extractant by using the second non-solvent beneficially increases the amount of hemicellulose extracted from the cellulosic material.

Amine Oxides

Amine oxides are chemical compounds that contain the functional group $R_3N^+$—$O^-$, which represents an N—O bond with three additional hydrogen and/or hydrocarbon side chains. Preferably, the amine oxide employed in the invention comprises a tertiary amine (tertiary amine N-oxide). In one embodiment, amine oxides that are stable in water can be used.

In some embodiments, the amine oxide may be selected from a group consisting oxides of trimethylamine, triethylamine, tripropylamine, monomethyldiethylamine, dimethylmonoethylamine, monomethyldipropylamine, N-dimethyl-, N-diethyl- or N-dipropylcyclohexylamine, N-dimethylmethylcyclohexylamine, pyridine, and pyridine N-oxide. In some embodiments, the amine oxide may be a cyclic mono (N-methylamine-N-oxide) compound such as n-methylmorpholine n-oxide (NMMO). In some embodiments, the amine oxide may be $R_1R_2R_3N$—O, wherein $R_1$, $R_2$ and $R_3$ are alkyl chains with chain length from 1 to 12.

It is known that NMMO monohydrate may be used as a solvent in the Lyocell process to produce Tencel fiber. Typically, cellulose is insoluble in most solvents because of its strong and highly structured intermolecular hydrogen bonding network. NMMO is able to break the hydrogen bonding network that keeps cellulose insoluble to in solvents. Therefore, the use of NMMO alone would destroy the fiber morphology of cellulose. It has now been discovered that by using the proper ratio of an amine oxide, such as NMMO, with a non-solvent, α-cellulosic components in the cellulosic material may be beneficially preserved and the fiber morphology retained.

Non-Solvent

As stated above, non-solvents in the context of this invention include solvents that do not have the ability to readily dissolve α-cellulose. In exemplary embodiments, the non-solvent is selected from the group consisting of water, alcohols such as methanol, ethanol, n-propanol, isopropanol, n-butanol, tert-butanol, diols and polyols such as ethanediol and propanediol, amino alcohols such as ethanolamine, diethanolamine and triethanolamine, aromatic solvents, e.g. benzene, toluene, ethylbenzene or xylenes, halogenated solvents, e.g. dichloromethane, chloroform, carbon tetrachloride, dichloroethane or chlorobenzene, aliphatic solvents, e.g. pentane, hexane, heptane, octane, ligroin, petroleum ether, cyclohexane and decalin, ethers, e.g. tetrahydrofuran, diethyl ether, methyl tert-butyl ether and diethylene glycol monomethyl ether, ketones such as acetone and methyl ethyl ketone, esters, e.g. ethyl acetate, dimethyl carbonate, dipropyl carbonate, propylene carbonate, amides, e.g., formamide, dimethylformamide (DMF), dimethylacetamide, dimethyl sulfoxide (DMSO), acetonitrile and mixtures thereof.

In one embodiment, a second non-solvent may be used in conjunction with the first non-solvent and the amine oxide as described above. In one embodiment, the second non-solvent decreases the viscosity of the extractant. In one embodiment, the second non-solvent has a viscosity of less than 2.0 mPa·s at 25° C. In one embodiment, the second non-solvent is selected from the group consisting of formamide, dimethylformamide (DMF), dimethylacetamide, dimethyl sulfoxide (DMSO), N-methylpyrrolidone, propylene carbonate, acetonitrile and mixtures thereof. It is postulated that using a low viscosity second non-solvent in the extractant, a smaller amount of amine oxide is needed to extract the hemicellulose in the cellulosic material.

Washing Agent

In one embodiment, the cellulosic product is washed using a washing agent after the hemicellulose is extracted therefrom in the extractant. The primary purpose of the washing step is to remove residual extractant from the cellulose product as well as remove loosely bound hemicellulose contained therein. The washing agent preferably comprises a non-solvent, which cleanses the cellulose product, but may also include some low level of extractant resulting from the sequence of washing steps. In one embodiment, the washing agent is selected from the group consisting of water, alcohols, polyols, amino alcohols, aromatic solvents, halogenated solvents, aliphatic solvents, ethers, ketones, esters, formamide, dimethylformamide (DMF), dimethylacetamide, propylene carbonate, dimethyl sulfoxide (DMSO), acetonitrile and mixtures thereof. In an one embodiment, the washing agent is selected from the group consisting of DMSO, DMF, N-methylpyrrolidone, methanol, ethanol, isopropanol, dimethyl carbonate, propylene carbonate, acetone, water, and mixtures thereof.

Enzyme

As discussed above, in one embodiment, the cellulosic material is treated with an enzyme, preferably a hemicellulase, to break down residual hemicellulose contained in the cellulosic material. The hemicellulase includes one or more enzymes that hydrolyze hemicellulose to form simpler sugars, ultimately yielding monosaccharides (e.g., glucose, other hexoses, pentoses). Suitable hemicellulase include one or more of xyloglucanase, β-xylosidase, endoxylanase, α-L-arabinofuranosidase, α-glucuronidase, and acetyl xylan esterase. Preferably, the enzymes include a combination of both endo-enzymes (i.e., enzymes hydrolyzing internal polysaccharide bonds to form smaller poly- and oligosaccharides) and exo-enzymes (i.e., enzymes hydrolyzing terminal and/or near-terminal polysaccharide bonds) to facilitate the rapid hydrolysis of large polysaccharide molecules. Suitable commercial hemicellulase include SHEARZYME (available from Novozymes A/S, Bagsvaerd, Denmark), PULPZYME (available from Novozymes A/S, Bagsvaerd, Denmark), FRIMASE B210 (available from Puratos, Groot-Bijgaarden, Belgium), FRIMASE B218 (available from Puratos, Groot-Bijgaarden, Belgium), GRINDAMYL (available from Danisco, Copenhagen, Denmark), ECOPULP TX200A (available from AB Enzymes, Darmstadt, Germany), MULTIFECT Xylanase (available from Genencor/Danisco, Palo Alto, USA), PENTOPAN Mono BG (available from Novozymes, Bagsvaerd, Denmark), and PENTOPAN 500 BG (available from Novozymes, Bagsvaerd, Denmark).

The enzymes generally can be used in amounts that are not particularly limited. For example, hemicellulase can be used in amounts ranging from about 0.001 mg/g to about 500 mg/g (e.g., about 0.05 mg/g to about 200 mg/g, about 0.1 mg/g to about 100 mg/g, about 0.2 mg/g to about 50 mg/g, or about 0.3 mg/g to about 40 mg/g). The concentration units are milligrams of enzyme per gram of cellulosic material.

Processing Steps

In the process of the present invention, a cellulosic material is treated with an extractant, which includes an amine oxide and a non-solvent. The hemicellulose is dissolved in the extractant, and the resulting extracted hemicellulose is separated from the cellulosic material. After the extraction step, the cellulosic material is optionally washed with a washing agent. The extracted cellulosic material, i.e. cellulose product is recovered for further use. In another embodiment, the extractant is recovered and may be recycled. In another embodiment, the process may further include enzymatic digestion of hemicellulose, extraction and/or isolation of digested hemicellulose and recovery of a cellulosic product with a reduced amount of hemicellulose.

One suitable treatment comprises extracting the cellulosic material with the extractant to selectively dissolve hemicellulose, and thereafter separating the dissolved hemicellulose in the liquid phase from the solid cellulosic product. The solid cellulosic product retains a cellulosic fiber morphology.

In the extraction step, the solid/liquid ratio may range from 0.5/100 to 1/6, depending largely on the extraction apparatus and set-up employed. In batch processes, a solid/liquid ratio of 1.25/100 may be used to facilitate the filtration. In a countercurrent extraction process, a solid/liquid ratio of 1/10 to 1/6 may be used.

In one embodiment, the solid cellulosic product may be washed using a washing agent, e.g., washing solution, which may have the property of dissolving hemicellulose and/or removing residual extractant. Therefore, any remaining hemicellulose and/or residual extractant in the cellulosic product may be dissolved and removed during the washing step.

In one embodiment, the cellulosic product may be subjected to repeat extraction. For example, the cellulosic product may be treated with the extractant after the initial extraction step to further extract any remaining hemicellulose. In one embodiment, the cellulosic product may be treated with the extractant for a second time after the washing step. In some embodiments, the cellulosic product may be subjected to a third or fourth extraction step.

In one embodiment, the cellulosic material may be subjected to enzyme treatment. For example, the cellulosic material may be treated with an enzyme after the extraction step. It has now been discovered that more hemicellulose is removed from the cellulosic material when the cellulosic material is first treated with the extractant. Without being bound by theory, by treating the cellulosic material first with the extractant, the enzyme may penetrate the cellulosic material more easily to hydrolyze the hemicellulose. In comparison, less hemicellulose is removed from the cellulosic material when it is first treated by with an enzyme followed by extraction.

In one embodiment, after treating with extractant and enzyme, the cellulosic product may be treated with the extractant again to further remove additional hemicellulose.

Washing

In one embodiment, the cellulosic material may be washed using a washing agent to wash and remove hemicellulose and/or enzyme. In one embodiment, the cellulosic material may be washed between extraction treatments. The cellulosic material may be washed between extraction treatment and enzyme treatment. In one embodiment, the washing agent may be selected from the group consisting of dimethylformamide (DMF), dimethyl sulfoxide (DMSO), N-methylpyrrolidone, dimethyl acetamide, dimethyl carbonate, propylene carbonate, water, and mixtures thereof.

The treatment of the cellulosic material may be conducted at an elevated temperature, and preferably at atmospheric pressure or slightly above atmospheric pressure. Preferably the contacting is conducted at a temperature from 30° C. to 150° C., e.g., from 50° C. to 130° C., or from 70° C. to 120° C. In terms of upper limit, the treatment of the cellulosic material may be conducted at a temperature of less than 150° C., e.g., less than 130° C., or less than 120° C. In terms of lower limit, the treatment of the cellulosic material may be conducted at a temperature of greater than 30° C., e.g., greater than 50° C., or greater than 70° C. The pressure is in the range from 100 kPa to 150 kPa, preferably from 100 kPa to 120 kPa, more preferably from 100 kPa to 110 kPa.

The cellulosic material may contact the extractant from 5 minutes to 180 minutes, e.g., from 40 minutes to 150 minutes, or from 60 minutes to 90 minutes. In terms of lower limits, the treatment of the cellulosic material may be contacted for at least 5 minutes, e.g., at least 10 minutes or at least 20 minutes. In terms of upper limits, the treatment of the cellulosic material may be contacted for at most 180 minutes, e.g., at most 150 minutes, at most 120 minutes, or at most 60 minutes.

The extraction process may be conducted in a batch, a semi-batch or a continuous process with material flowing either co-current or counter-current in relation to one another. In a continuous process, the cellulosic material contacts the extractant in one or more extraction vessels. In one embodiment, the extractant may be heated to the desired temperature before contacting the cellulosic materials. In one embodiment, the extraction vessel(s) may be heated by any suitable means to the desired temperature.

Counter-Current Extraction

The amount of extractant required has a significant impact on process economics. Counter-current extraction may achieve greater extraction efficiency while maintaining a reasonable extractant usage requirement. Counter-current extraction of solubles from pulp can be accomplished in a variety of commercial equipment such as, but not limited to agitated tanks, hydrapulpers and screw extractors. Twin-screw extractors are generally more efficient than single-screw extractors. Suitable commercial equipment to effect the separation of solid and liquid phases after extraction includes filters, centrifuges, and the like.

Good liquid/solid contact during extraction also depends on the drainage characteristics of the pulp. The particle size of pulp may be important in continuous counter-current extraction because very fine particles tend to compact and cause liquid to channel or block liquid flow completely. Extractant temperature may also have an effect on the extraction of solubles from the pulp.

Rinsing and Drying

The cellulose product may be rinsed using a rinsing agent to remove the extractant, enzyme, or dissolved hemicellulose. In one embodiment, the rinsing agent may be selected from the group consisting of water, alcohols, polyols, amino alcohols, aromatic solvents, halogenated solvents, aliphatic solvents, ethers, ketones, esters, formamide, dimethylformamide (DMF), dimethylacetamide, propylene carbonate, dimethyl sulfoxide (DMSO), acetonitrile and mixtures thereof. Specifically, acetone may be use at a last rinsing agent to remove traces of water or other chemicals from the cellulose product.

Cellulose Product

In accordance to the present invention, high purity α-cellulose product is produced. In particular, these high purity α-cellulose products are high purity dissolving grade pulps with less than 5 wt. % hemicellulose. The purity of the α-cellulose may be indicated by a lower absorbance value at a certain wavelength. In one embodiment, for example, the cellulosic product has an absorbance of less than 2.0 at 277 nm, e.g., less than 1.6 at 277 nm, or less than 1.2 at 277 nm. Paper grade pulp, in contrast, typically has an absorbance of greater than 4.7 at 277 nm.

In addition to retaining the fiber morphology of the cellulosic product, the high purity α-cellulose grade pulp product also retains other characteristics such as intrinsic viscosity and brightness. The high purity α-cellulose grade pulp product may be further processed to make cellulose derivatives, such as cellulose ether, cellulose esters, cellulose nitrate, other derivatives of cellulose, or regenerated cellulose fiber, such as viscose, lyocell, rayon, etc. Preferably, the high purity α-cellulose grade pulp may be used to make cellulose acetate.

EXAMPLES

Determining Hemicellulose Content Using UV/Vis

Example 1

A novel method using UV/Vis analysis method for fast determination of hemicellulose content in a sample was developed. Hemicellulose includes xylan, glucuronoxylan, arabinoxylan, glucomannan, galactomannan, and xyloglucan, while α-cellulose includes glucose. The UV/Vis analysis method is based on the fact that under the pre-hydrolysis conditions xylan degrades to form 2-furfural and glucose degrades to form 5-hydroxymethyl-2-furfural. Because the rate of degradation of the monosaccharide is different, the difference in rate of formation of furfural compounds may be used as the fundamental basis for UV/Vis method.

The UV/Visable spectrum method includes a first step of pre-hydrolyzing the sample in sulfuric acid (72 wt. %) for 60±2 min at 30° C. Depending on the concentration of xylan in the sample, 10 ml or 5 ml of deionized water were added to the pre-hydrolysis solution. The solution is was then measured at 270 nm to 280 nm with a SHIMADZU UV/Vis spectrometer UV-2600. The final results were adjusted by the dilution factor of the DI water dilution.

Extraction with N-methylmorpholine N-oxide (NMMO)/$H_2O$ Extractant Binary System Example 2

0.5 gram of paper grade pulp sample was weighed and put into a 75 ml glass vial with Teflon face lined cap. A pre-calculated amount of NMMO and $H_2O$ (total) were added into the glass vial according to the predetermined extractant weight ratio (NMMO/$H_2O$) and mixed well with the pulp samples. The sample thus contained a solid/liquid ratio (S/L) of 1.25:100. The glass vials with pulp and extractant solution were placed into a NAPCO® Autoclave (Model 800-DSE autoclave), and the autoclave was set at 120° C. for 1 hr. After the autoclave treatment, the glass vial was left to cool to room temperature.

The content in the glass vial was transferred to a Buchner funnel with a 5 μm twilled Dutch wire cloth filter pads and filtered under vacuum until less than one liquid drop came out of the funnel in a minute. The pulp formed a thin sheet of paper on the pads.

20 ml fresh DMSO solvent was added to the filter pads and were filtered under vacuum again until less than one liquid drop came out of the funnel in a minute. The color of the pad was checked to ensure that the pulp was white without any color. Additional 20 ml of fresh DMSO was added to wash the sample and the sample was placed under vacuum. The process was repeated until the pulp appeared to be white without any color.

Following the DMSO wash, the pulp sheet from the filter pads was dispersed in 40 to 100 ml of water, and then filtered again. This water wash generally was conducted 4 times. 20 ml of acetone was added to the pulp sheet on the filter pads and then a vacuum was applied to dry. The pulp sheet was left to dry overnight in a chemical hood.

In some experiments, the extracted pulp samples were subjected to the extraction process again to further improve their purity. In some experiments, instead of the DMSO solvent, the extractant composition (NMMO/$H_2O$) was used to extract the sample for one or more times. Water was used to wash away the extractant composition.

Example 3

The results for the amount of hemicellulose in the paper pulp product using the above-described NMMO/$H_2O$ binary extractant treatment are shown in Table 1. The absorbance of a commercially available hardwood acetate grade pulp was used as a bench mark. The absorbance of a hardwood paper grade pulp starting material was also measured and used as a comparison.

TABLE 1

| NMMO/$H_2O$ Binary Extractant on Hardwood Paper Grade Pulp | |
|---|---|
| Extractant Composition by wt. % | Absorbance at 277 nm |
| Astracel ECF (Paper Grade Pulp) without treatment | 4.826 |
| 50 NMMO/50 $H_2O$ | 4.608 |
| 55 NMMO/45 $H_2O$ | 4.525 |
| 60 NMMO/40 $H_2O$ | 4.280 |
| 65 NMMO/35 $H_2O$ | 3.740 |
| 70 NMMO/30 $H_2O$ | 3.560 |
| 75 NMMO/25 $H_2O$ | 2.926 |
| 80 NMMO/20 $H_2O$ | 1.575 |
| 85 NMMO/15 $H_2O$ | 4.339 |

TABLE 1-continued

NMMO/$H_2O$ Binary Extractant on Hardwood Paper Grade Pulp

| Extractant Composition by wt. % | Absorbance at 277 nm |
|---|---|
| Commercially Available Acetate Grade Pulp (Benchmark) | 0.887 |

As shown in Table 1, the use of over 40 wt. % or less than 15 wt. % water in the NMMO/$H_2O$ binary extractant system appears to have minimal effect in removing hemicellulose from the hardwood paper grade pulp. Surprisingly and unexpectedly, the use of about 20 wt. % water in the NMMO/$H_2O$ binary extractant system removed the greatest amount of hemicellulose without compromising the fiber morphology of the paper grade pulp. The resulting purified pulp product desirably had a low (1.575) absorbance level.

Example 4

Table 2 shows the results for the amount of hemicellulose for the treatment of paper grade pulp using NMMO/$H_2O$ binary extractant system on softwood. The absorbance of softwood paper grade pulp starting material was also measured and used as a comparison.

TABLE 2

NMMO/$H_2O$ Binary Extractant System on Softwood Paper Grade Pulp

| Extractant Composition by wt. % | Absorbance at 277 nm |
|---|---|
| Paper Grade Pulp without treatment | 1.754 |
| 50 NMMO/50 $H_2O$ | 1.748 |
| 55 NMMO/45 $H_2O$ | 1.748 |
| 60 NMMO/40 $H_2O$ | 1.494 |
| 65 NMMO/35 $H_2O$ | 1.367 |
| 70 NMMO/30 $H_2O$ | 1.08 |
| 75 NMMO/25 $H_2O$ | 0.843 |
| 80 NMMO/20 $H_2O$ | 1.337 |

As shown in Table 2, the use of less than 55 wt. % NMMO in the NMMO/$H_2O$ binary extractant system appeared to have no effect in removing hemicellulose from the softwood paper grade pulp. As more NMMO is used, absorbance decreased, suggesting that more hemicellulose was removed from the softwood paper grade pulp. Surprisingly and unexpectedly, the use of 75 wt. % NMMO in the NMMO/$H_2O$ binary extractant system resulted in a purified paper grade pulp product that had a lower absorbance than 70 wt. % NMMO/30 wt. % $H_2O$ and 80 wt. % NMMO/20 wt. % $H_2O$. This result suggests that by using an appropriate mixture of amine oxide (NMMO) and water a maximum amount of hemicellulose may be removed from the softwood paper grade pulp.

Example 5

Figure 1:
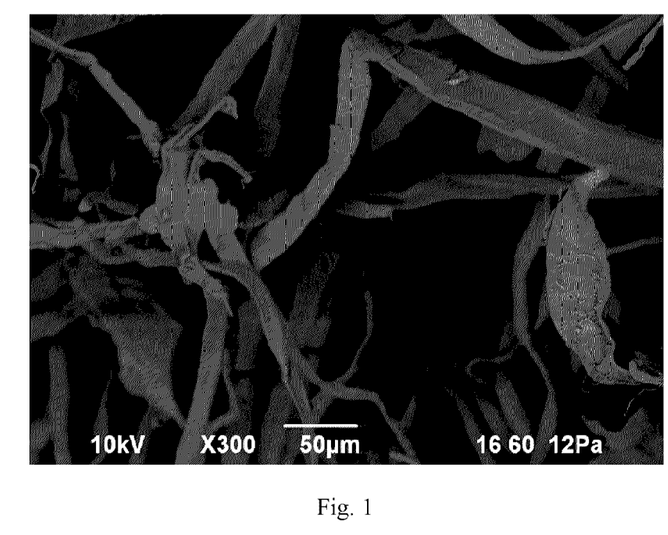
FIG. 1 shows the structure and morphology of a pre-treated hardwood paper grade pulp.
Figure 2:
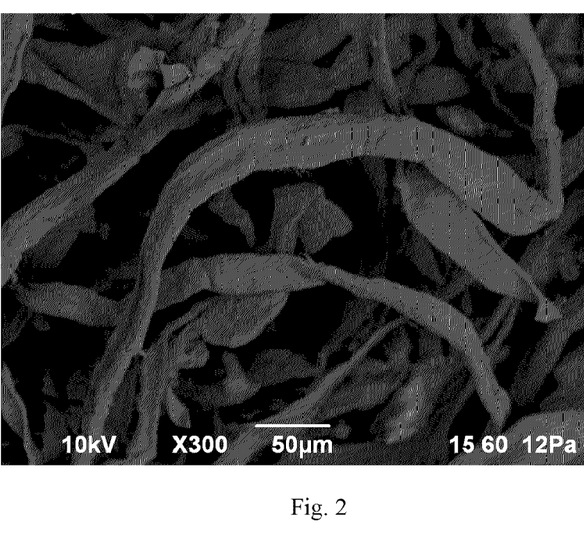
FIG. 2 shows the structure and morphology of a pre-treated softwood paper grade pulp.
Figure 3:
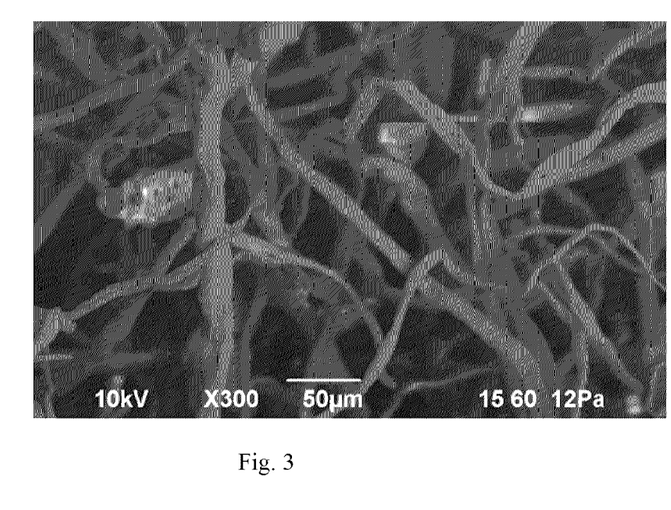
FIG. 3 shows the structure and morphology of a reduced hemicellulose cellulosic product obtained using the inventive method.
Figure 4:
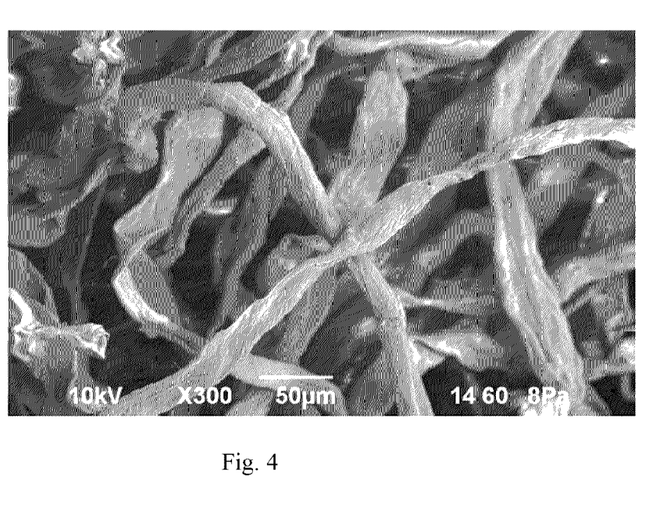
FIG. 4 shows the structure and morphology of a reduced hemicellulose cellulosic product obtained using the inventive method.
Figure 5:
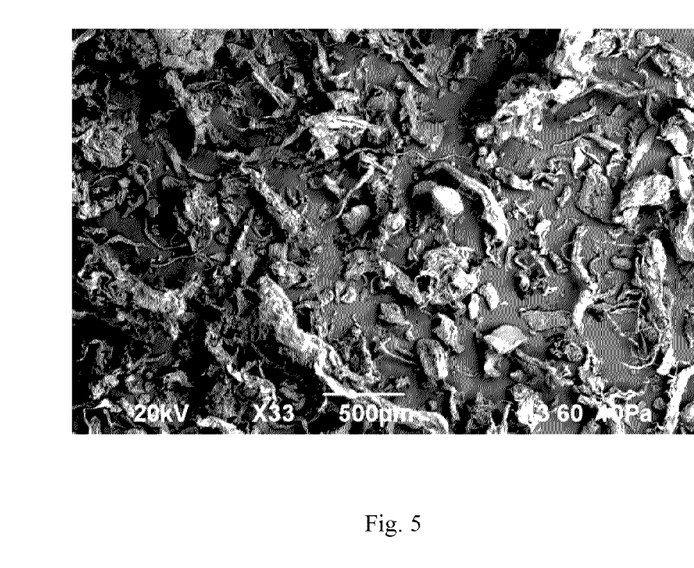
FIG. 5 shows the structure and morphology of a hardwood paper grade pulp treated with an amine oxide and reconstituted using a non-solvent.
Figure 6:
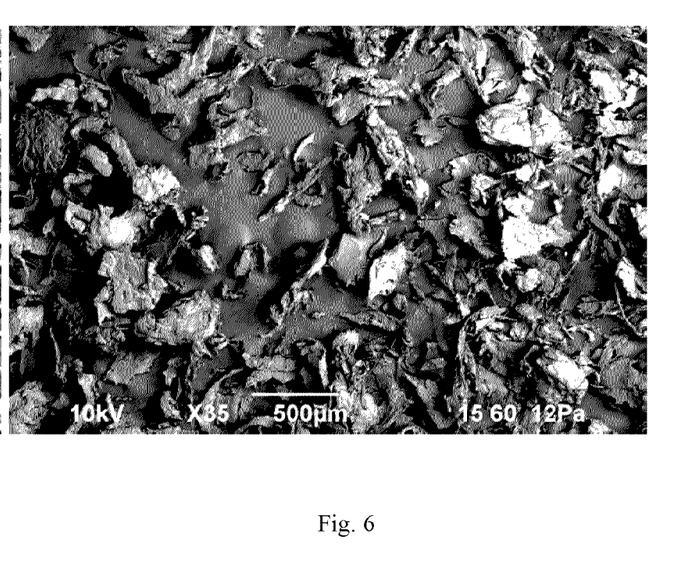
FIG. 6 shows the structure and morphology of a softwood paper grade pulp treated with an amine oxide and reconstituted using a non-solvent.

The paper grade pulp fiber morphology was investigated with scanning electron microscopy (SEM). FIG. 1 shows the SEM micrograph for a starting material hardwood paper grade pulp and FIG. 2 shows the SEM micrograph for a starting material softwood paper grade pulp. The fiber morphology of the hardwood pulp and softwood pulp are observed in these SEM micrographs. The starting material paper grade pulps were treated with the methods of the instant invention. FIGS. 3 and 4 show SEM micrographs for the hardwood paper grade pulp and the softwood paper grade pulp after the treatment, respectively. As shown in FIGS. 3 and 4, the wood fiber morphology for both hardwood and softwood remained intact, although some small pores were observed due to the selective removal of hemicellulose from the fiber structure. This porous fiber morphology is advantageous for downstream cellulose derivatization such as acetylation, etherification, or nitration by providing additional physical access route to chemical reagents. FIGS. 5 and 6 show SEM micrographs for the hardwood paper grade pulp and the softwood paper grade pulp, respectively, treated using an amine oxide and regenerated using a non-solvent. As shown in both figures, the fiber morphology of the cellulosic structure is destroyed. The figures demonstrate the benefits of using the solvent systems of the present invention to obtain high purity α-cellulose and retaining its fiber morphology.

Example 6

In addition to paper grade pulp, experiments were also conducted using viscose pulp. Table 3 compares two different viscose pulps and their treatment using the 75 wt. % NMMO/25 wt. % $H_2O$ binary extractant system. The amount of hemicellulose in the samples are measured using the procedure in Example 1 and are shown in Table 3.

TABLE 3

75 wt. % NMMO/25 wt. % $H_2O$ Binary Extractant System Treatment of Viscose Pulp Absorbance at 277 nM

| | Untreated | Treated |
|---|---|---|
| Commercial Viscose I | 1.11 | 0.88 |
| Commercial Viscose II | 0.93 | 0.77 |
| Commercially Available Hardwood Acetate Pulp (Control) | 0.79 | — |

Table 3 shows that in addition to using paper grade pulp as starting materials, the present invention may also use other starting materials, such as viscose pulp. Commercial viscose pulps by two different manufacturers were treated using the NMMO/$H_2O$ binary extractant system. The data shows that by treating the viscose pulp with a binary extractant system of 75 wt. % NMMO/25 wt. % $H_2O$, the treated pulp product had a level of hemicellulose that is similar to the commercially available acetate grade pulp. The invention is accordingly applicable to other pulp starting materials in addition to paper grade pulp, such as viscose grade pulp, fluff grade pulp, or acetate grade pulp for extremely high purity applications.

Extraction with NMMO/$H_2O$/DMSO Tertiary Extractant System

Example 6

0.5 gram of paper grade pulp sample was weighed and put into a 75 ml glass vial with Teflon face lined cap. NMMO/$H_2O$ (75/25 wt. %/wt. %) and DMSO were added into the glass vial according to the predetermined extractant weight ratio and mixed well with pulp samples. This provided a solid/liquid ratio (S/L) of 1.25:100. The glass vials with pulp and extractant solution were placed into a NAPCO® Autoclave (Model 800-DSE autoclave), and the autoclave was set at 120° C. for 1 hr. After the autoclave treatment, the glass vial was left to cool to room temperature.

The content in the glass vial was transferred to a Büchner funnel with a 5 μm twilled Dutch wire cloth filter pads and filtered under vacuum until less than one liquid drop comes out of the funnel in a minute. The pulp formed a thin sheet of paper on the pads.

20 ml fresh DMSO solvent were added to the filter pads followed by filtering under vacuum until less than one liquid drop came out of the funnel in a minute. The color of the pad was checked to ensure that the pulp was white without any color. An additional 20 ml of fresh DMSO were added to wash the sample and the sample was placed under vacuum. The process was repeated until the pulp appeared to be without any color.

Following DMSO wash, the pulp sheet from the filter pads were dispersed in 40 to 100 ml of water, and then filtered again. This water wash was generally conducted 4 times. Then 20 ml of acetone were added to the pulp sheet on the filter pads and vacuum was applied to dryness. The pulp sheet was left dry in a chemical hood overnight.

In some experiments, the extracted pulp samples were subjected to the extraction process again to further improve its purity. In some experiments, instead of the DMSO solvent, the extractant composition (NMMO/$H_2O$) was used to extract the sample one or more times. Water was used to wash away the extractant composition.

Example 7

The results for the amount of hemicellulose in the paper pulp product using the above-described NMMO/$H_2O$/DMSO tertiary extractant system are shown in Table 4. The absorbance of commercially available acetate grade pulp and the starting material paper grade pulp, are provided as references. The amount of hemicellulose in the samples was measured using the procedure in Example 1 and are shown in Table 4.

TABLE 4

NMMO/$H_2O$/DMSO Tertiary Extractant System
Treatment on Hardwood Paper Grade Pulp

| Extractant Composition by wt. % | Absorbance at 277 nm |
|---|---|
| Commercially Available Acetate Grade Pulp | 0.851 |
| Paper Grade Pulp (without treatment) | 4.891 |
| 100 [75 NMMO/25 $H_2O$]/0 DMSO | 1.314 |
| 50 [75 NMMO/25 $H_2O$]/50 DMSO | 1.095 |
| 37.5 [75 NMMO/25 $H_2O$]/62.5 DMSO | 1.223 |
| 25 [75 NMMO/25 $H_2O$]/75 DMSO | 1.095 |
| 12.5 [75 NMMO/25 $H_2O$]/87.5 DMSO | 1.271 |
| 2.5 [75 NMMO/25 $H_2O$]/97.5 DMSO | 2.885 |

The extractant compositions used in Table 4 were 75 wt. % NMMO/25 wt. % $H_2O$ combined with different weight percentages of DMSO. This example illustrates the effect of DMSO in the extractant system. As shown in Table 4, by using 0 wt. % DMSO, the absorbance of the sample dropped from 4.891 to 1.314. This suggests that the use of 75 wt. % NMMO/25 wt. % $H_2O$ beneficially extracted hemicellulose from the hardwood paper grade pulp. It appears that more hemicellulose is removed from the hardwood paper grade pulp when DMSO is used in the extractant system. Specifically, the use of 50-87.5 wt. % DMSO reduced the absorbance to 1.095. Surprisingly and unexpectedly, the use of 62.5 wt. % DMSO in combination with 75 wt. % NMMO/25 wt. % $H_2O$ resulted in a slight increase in absorbance. More interestingly, the use of 97.5 wt. % DMSO appeared to remove less hemicellulose than the use of 87.5 wt. % DMSO. This result suggests that an appropriate mixture of amine oxide (NMMO), water, and DMSO is necessary to remove a maximum amount of hemicellulose from the hardwood paper grade pulp.

Example 8

Table 5 shows the results for the treatment of hardwood paper grade pulp using the procedure of Example 6, with NMMO monohydrate (one mole of NMMO and one mole of water) diluted in 90-99 wt. % DMSO. The absorbance of a hardwood paper grade pulp starting material was also measured and used as a comparison.

TABLE 5

NMMO/H2O/DMSO Extractant on Hardwood Paper Grade Pulp

| Extractant Composition by wt. % | Absorbance at 277 nm |
|---|---|
| Hardwood Paper Grade Pulp without treatment | 4.826 |
| 100 DMSO | 4.674 |
| 1 [86.7NMMO/13.3$H_2O$]/99 DMSO | 3.53 |
| 2.5[86.7NMMO/13.3$H_2O$]/97.5 DMSO | 2.19 |
| 5[86.7NMMO/13.3$H_2O$]/95 DMSO | 1.30 |
| 8[86.7NMMO/13.3$H_2O$]/92 DMSO | 1.06 |
| 10[86.7NMMO/13.3$H_2O$]/90 DMSO | 1.15 |
| Commercially Available Acetate Grade Pulp (Benchmark) | 0.887 |

The extractant compositions used in Table 5 were NMMO monohydrate combined with different weight percentages of DMSO. This example illustrates the effect of DMSO in the extractant system. As shown in Table 5, by using 100 wt. % DMSO, the absorbance of the sample changed slightly from 4.826 to 4.674. This suggests that DMSO alone is not an effective solvent for removing hemicellulose. At 1 wt. % NMMO monohydrate/99 wt. % DMSO, the absorbance reduced to 3.53. When NMMO monohydrate was increased to 8 wt. % and 10 wt. %, the absorbance reduced to 1.06 and 1.15, respectively. This suggests that by using 8 to 10 wt. % of NMMO monohydrate in DMSO, a maximum amount of hemicellulose may be extracted from the hardwood paper grade pulp.

Example 9

Table 6 shows the results for the treatment of softwood paper grade pulp using the procedure of Example 6, with NMMO monohydrate diluted in 90-99 wt. % DMSO. The absorbance of a softwood paper grade pulp starting material was also measured and used as a comparison.

TABLE 6

NMMO/$H_2O$/DMSO Extractant on Softwood Paper Grade Pulp

| Extractant Composition by wt. % | Absorbance at 277 nm |
|---|---|
| softwood Paper Grade Pulp without treatment | 2.66 |
| 1[86.7NMMO/13.3$H_2O$]/99 DMSO | 1.97 |
| 2.5[86.7NMMO/13.3$H_2O$]/97.5 DMSO | 1.48 |
| 5[86.7NMMO/13.3$H_2O$]/95 DMSO | 1.03 |
| 8[86.7NMMO/13.3$H_2O$]/92 DMSO | 0.84 |
| 10[86.7NMMO/13.3$H_2O$]/90 DMSO | 0.88 |
| Commercially Available Softwood Acetate Grade Pulp (Benchmark) | 0.86 |

Table 6 shows one mole of NMMO and one mole of water diluted in different concentrations of DMSO. As shown, the use of 1 wt. % NMMO monohydrate/99 wt. % DMSO beneficially reduced the absorbance from 2.66 to 1.97 at 277 nm.

In comparison, the use of 8 wt % NMMO monohydrate in DMSO reduced the absorbance to 0.84, which is lower than the absorbance of commercially available softwood acetate. This suggests that by modifying the concentration of NMMO and water in DMSO, a maximum amount of hemicellulose may be removed from the softwood paper grade pulp.

Enzyme Treatment

Example 10

Unless noted otherwise, hydrolysis was carried out for 4 hours at 40° C., pH 4.8, and a volume of 12.5 μL of the commercial Pulpzyme® enzyme solution for 0.5 g or pulp at a concentration of 60 mg/mL of pulp, with mixing at 900 rpm. Sugar was detected with the standard DNS assay and the pulp purity was monitored with the UV/Vis test method described above.

Example 11

Samples of hardwood paper pulp were subjected to enzyme treatment using Pulpzyme and NMMO/H$_2$O treatment [25 wt. % NMMO/75 wt. % H$_2$O]. The amount of hemicellulose in the sample was normalized to 100% using the Astracel ECF as a standard.

TABLE 7

NMMO/H$_2$O Binary Extractant System Treatment and
Enzyme Treatment on Hardwood Paper Grade Pulp

| Samples | Absorbance @ 277 nm |
| --- | --- |
| Paper Grade Pulp without treatment | 4.86 |
| Pulpzyme Treatment | 4.34 |
| NMMO/H$_2$O Treatment | 1.68 |
| NMMO/H$_2$O Treatment followed by Pulpzyme Treatment | 1.46 |
| NMMO/H$_2$O Treatment followed by Pulpzyme Treatment then NMMO/H$_2$O Treatment | 1.34 |
| Commercially Available Acetate Grade Pulp | 0.851 |

As shown in Table 7, the use of enzyme alone removed some hemicellulose from the paper grade pulp. The absorbance was reduced from 4.86 to 4.34. In comparison, the use of the extractant system according to the invention significantly reduced the absorbance from 4.86 to 1.68. By treating the paper grade pulp with the extractant system followed by enzyme, additional hemicellulose was removed and the absorbance was further reduced from 1.68 to 1.46. The paper grade pulp may be treated with the extractant system again after an initial extractant system and enzyme treatment. This repeated treatment resulted in the reduction of absorbance from 1.46 to 1.34.

Example 12

A multi-stage extraction was performed in order to simulate counter-current extraction. All extraction operations were carried out for 1 hour in a bath heated to 95° C.±2° C. An 8.0% NMMO/H$_2$O/DMSO solution was evaluated as the extractant. After 1 hour of extraction, the reaction mixture was cooled to room temperature and centrifuged in an MR23i Centrifuge from Thermo Scientific to separate the extraction solvents (filtrate) and the pulp. Both pulps and extraction solvents were then recycled, to obtain the representative final pulp and extraction solvent.

In particular, a first extraction was performed solely to obtain a filtrate, to be used in a second extraction. Thus, following a first extraction of 0.4 grams of Pulp A and 16 grams of fresh solvent, the reaction mixture was centrifuged to provide Filtrate 1A. Pulp A', the other product of the first extraction, was discarded for, as noted above, the first extraction was performed solely to obtain Filtrate 1A. Following the second extraction of 0.4 grams of Pulp B (from the same batch as Pulp A) and 16 grams of Filtrate 1A from the first extraction, the reaction mixture was centrifuged to provide Pulp B', to be used in a third extraction. Filtrate 2B, the other product of the second extraction, was discarded as representing the filtrate coming out of the counter-current extraction before the process reaches steady state. Following the third extraction of 0.4 grams of Pulp B' (from the second extraction) and 16 grams of fresh solvent, the reaction mixture was centrifuged to provide Pulp B", which represents the final pulp.

Filtrate 3B, the other product of the third extraction, in an amount of 16 grams, was then used in a fourth extraction of 0.4 grams of Pulp C (from the same batch as Pulp A and B), and the reaction mixture was centrifuged to provide Filtrate 4C, which represents the final extractant. Pulp C', the other product of the fourth extraction, was discarded as representing pulp coming out of the counter-current extraction before the process reaches steady state.

The UV-Vis purity of the pulp and comparative direct extraction (i.e., single extraction for 1 hour in a bath heated to 95° C.±2° C., followed by cooling to room temperature and centrifugation in an MR23i Centrifuge from Thermo Scientific to separate the filtrate and the pulp) results are summarized in Table 8, below.

TABLE 8

Comparative UV-Vis results of purified
pulp (S/L = 2.5%, 8% NMMO/H$_2$O/DMSO)

| | UV Absorbance @ 278 nm | |
| --- | --- | --- |
| Sample | Direct Extraction S/L = 2.5: 100, 8.0% NMMO/H$_2$O/DMSO | Multi-Stage Extraction S/L = 2.5: 100, 8.0% NMMO/H$_2$O/DMSO |
| 1 | 1.467 | 1.192 |
| 2 | 1.486 | 1.138 |
| 3 | 1.481 | 1.156 |
| 4 | 1.595 | 1.299 |
| Average | 1.478 | 1.162 |

Based on the results from Table 8, the UV-Vis absorbance of the purified pulp from 8.0 wt. % NMMO/H$_2$O/DMSO was reduced (i.e., from 1.48 to 1.16 for S/L=2.5:100) by multi-stage extraction versus direct extraction, indicating that counter extraction increased extraction efficiency. Without being bound by theory, extraction efficiency may depend on extractant solvation power to hemicellulose, and thus, when the extractant has high solvation power to hemicellulose, counter-current extraction could make full use of that extraction power to reduce the hemicellulose in the pulp and thus improve extraction efficiency.

While the invention has been described in detail, modifications within the spirit and scope of the invention will be readily apparent to those of skill in the art. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. A method for treating a cellulosic material, comprising:
   extracting the cellulosic material with an extractant to selectively extract hemicellulose, wherein the extractant comprises an amine oxide and a non-solvent; and
   separating the extracted hemicellulose from the cellulosic material to form a cellulosic product comprising less hemicellulose than the cellulosic material.

2. The method of claim 1, wherein the extractant selectively extracts at least 20% of hemicellulose in the cellulosic material.

3. The method of claim 1, wherein less than 15% of the cellulose in the cellulosic material is extracted.

4. The method of claim 1, wherein the cellulosic product retains a cellulosic fiber morphology.

5. The method of claim 1, wherein the amine oxide is selected from the group consisting of n-methylmorpholine n-oxide, pyridine N-oxide, $R_1R_2R_3N$—O, wherein $R_1$, $R_2$ and $R_3$ are alkyls with chain length from 1 to 12.

6. The method of claim 1, wherein the non-solvent is selected from the group consisting of water, dimethyl sulfoxide, dimethylformamide, alcohol, N-methylpyrrolidone, and mixtures thereof.

7. The method of claim 1, wherein the extractant comprises at least 50 wt. % amine oxide and at least 20 wt. % non-solvent.

8. The method of claim 1, wherein the extractant comprises at least 50 wt. % n-methylmorpholine n-oxide and at least 20 wt. % water.

9. The method of claim 1, wherein the extractant comprises at least 0.8 wt. % n-methylmorpholine n-oxide, at least 0.01 wt. % water, and at least 50 wt. % dimethyl sulfoxide.

10. The method of claim 1, further comprising treating the cellulosic product with an enzyme.

11. The method of claim 10, wherein the enzyme is a hemicellulase.

12. The method of claim 1, wherein the extracting step is conducted at a temperature from 30° C. to 150° C.

13. The method of claim 1, wherein the extracting step is between 5 minutes to 180 minutes.

14. The method of claim 1, further comprising washing the cellulosic product with at least one of dimethyl sulfoxide, dimethylformamide, N-methylpyrrolidone, methanol, ethanol, isopropanol, dimethyl carbonate, acetone and/or water.

15. The method of claim 1, wherein the cellulosic product has an absorbance of less than 2.0 at 277 nm.

16. The method of claim 1, wherein the cellulosic material comprises wood pulp.

17. The method of claim 16, wherein the cellulosic material comprises paper grade wood pulp.

18. The method of claim 16, wherein the cellulosic material comprises less than 90% α-cellulose.

19. The method of claim 1, wherein the extracting comprises batch, co-current, or counter-current extraction.

20. The method of claim 1, wherein the extracting comprises use of an agitated tank, hydrapulper, screw conveyor or screw extractor.

21. The method of claim 1, wherein solid and liquid phases are separated by a filter or centrifuge.

22. A method for producing high purity α-cellulose grade pulp, comprising:
   extracting hemicellulose from a wood pulp by treating the wood pulp with an extractant comprising an amine oxide and a non-solvent to form an intermediate wood pulp that retains a cellulosic fiber morphology;
   treating the intermediate wood pulp with an enzyme to hydrolyze the hemicellulose contained therein to form a reduced hemicellulose wood pulp; and
   washing the reduced hemicellulose wood pulp with a wash solution to form the high purity α-cellulose grade pulp.

23. The method of claim 22, wherein the high purity α-cellulose grade pulp has an absorbance of less than 1.5 at 277 nm.

24. The method of claim 22, wherein at least 50% of the hemicellulose is removed from the wood pulp.

25. The method of claim 22, further comprising repeating the extraction step to remove additional hemicellulose.

26. The method of claim 22, wherein the extracting comprises batch, co-current, or counter-current extraction.

27. The method of claim 22, wherein the extracting comprises use of an agitated tank, hydrapulper, screw conveyor or screw extractor.

28. The method of claim 22, wherein solid and liquid phases are separated by a filter or centrifuge.

* * * * *